(12) United States Patent
Ikeda et al.

(10) Patent No.: US 8,859,463 B2
(45) Date of Patent: *Oct. 14, 2014

(54) METHOD FOR CONTROLLING NOXIOUS ORGANISMS

(75) Inventors: Hajime Ikeda, Kobe (JP); Atsushi Iwata, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 257 days.

This patent is subject to a terminal disclaimer.

(21) Appl. No.: 12/767,612

(22) Filed: Apr. 26, 2010

(65) Prior Publication Data

US 2010/0317520 A1  Dec. 16, 2010

Related U.S. Application Data

(63) Continuation-in-part of application No. 12/562,957, filed on Sep. 18, 2009, now Pat. No. 8,242,052.

(30) Foreign Application Priority Data

Jun. 12, 2009 (JP) ................................ 2009-140959
Jul. 15, 2009 (JP) ................................ 2009-166508

(51) Int. Cl.
  *A01N 25/26* (2006.01)
  *A01N 43/40* (2006.01)
  *A01N 47/10* (2006.01)
  *A01N 43/60* (2006.01)
  *A01N 51/00* (2006.01)
  *A01N 43/653* (2006.01)

(52) U.S. Cl.
  CPC .............. *A01N 51/00* (2013.01); *A01N 43/653* (2013.01)
  USPC ............ 504/100; 504/130; 504/135; 504/136

(58) Field of Classification Search
  None
  See application file for complete search history.

(56) References Cited

FOREIGN PATENT DOCUMENTS

| WO | WO 00/27203 A1 | 5/2000 |
| WO | WO-0027203 | * 5/2000 |
| WO | WO 2005/009128 A1 | 2/2005 |
| WO | WO 03/096811 A1 | 11/2008 |

OTHER PUBLICATIONS

U.S. Office Action dated Nov. 17, 2011, for U.S. Appl. No. 12/562,957.

* cited by examiner

*Primary Examiner* — Alton Pryor
(74) *Attorney, Agent, or Firm* — Birch, Stewart, Kolasch & Birch, LLP

(57) ABSTRACT

A control method against noxious organisms in a field of soybean or corn, which comprises applying one or more PPO-inhibiting compounds selected from the group consisting of flumioxazin, sulfentrazone, saflufenacil, oxyfluorfen and 3-(4-chloro-6-fluoro-2-trifluoromethylbenzimidazol-7-yl)-1-methyl-6-trifluoromethyl-2,4-(1H,3H)pyrimidinedione to soil or weeds in the field where soybean or corn seeds have been sown or where said seeds are to be sown, said seeds being treated with one or more compounds selected from the group consisting of neonicotinoid compounds, azole compounds, strobilurin compounds and metalaxyl compounds.

18 Claims, No Drawings

METHOD FOR CONTROLLING NOXIOUS ORGANISMS

This application is a Continuation-in-Part of copending application Ser. No. 12/562,957 filed on Sep. 18, 2009, which claims priority to Application Nos. 2009-140959 and 2009-166508 filed in Japan, on Jun. 12, 2009 and Jul. 15, 2009. The entire contents of all of the above applications is hereby incorporated by reference into the present application respectively.

FIELD OF THE INVENTION

The present invention relates to a method for controlling noxious organisms, namely harmful arthropods, plant pathogens and weeds.

BACKGROUND OF THE INVENTION

A lot of compounds are known as active ingredients of noxious organism-controlling composition such as insecticides, bactericides or herbicides (Crop Protection Handbook, vol. 89 (2003), U.S. Pat. No. 6,077,812, or Crop Protection Handbook, vol. 95 (2009))

SUMMARY OF THE INVENTION

The present invention provides a method which shows excellent controlling effects on noxious organisms in a field of soybean or corn.

The present invention relates to the followings.

[1] A control method against noxious organisms in a field of soybean or corn which comprises applying one or more PPO-inhibiting compounds selected from the group consisting of flumioxazin, sulfentrazone, saflufenacil, oxyfluorfen and 3-(4-chloro-6-fluoro-2-trifluoromethylbenzimidazol-7-yl)-1-methyl-6-trifluoromethyl-2,4-(1H,3H) pyrimidinedione to soil or weeds in the field where soybean or corn seeds have been sown or where said seeds are to be sown, said seeds being treated with one or more compounds selected from the group consisting of neonicotinoid compounds, azole compounds, strobilurin compounds and metalaxyl compounds.

[2] A control method against noxious organisms in a field of soybean or corn, which comprises the steps of:
treating a soybean or corn seed with Compound I selected from the group consisting of neonicotinoid compounds, azole compounds, strobilurin compounds and metalaxyl compounds, and
treating the field with one or more PPO-inhibiting compounds selected from the group consisting of flumioxazin, sulfentrazone, saflufenacil, oxyfluorfen and 3-(4-chloro-6-fluoro-2-trifluoromethylbenzimidazol-7-yl)-1-methyl-6-trifluoromethyl-2,4-(1H,3H)pyrimidinedione before, at or after sowing the soybean or corn seed treated with Compound I.

[3] The control method according to [1] or [2], wherein the neonicotinoid compound is selected from the group consisting of clothianidin, thiamethoxam, imidacloprid, dinotefuran, nitenpyram, acetamiprid and thiacloprid.

[4] The control method acoording to [2] wherein Compound I is one or more neonicotinoid compounds selected from the group consisting of clothianidin, thiamethoxam, imidacloprid, dinotefuran, nitenpyram, acetamiprid and thiacloprid.

[5] The control method according to [1] or [2], wherein the neonicotinoid compound is clothianidin or thiamethoxam.

[6] The control method according to [5], wherein the PPO-inhibiting compound is flumioxazin, sulfentrazone or saflufenacil.

[7] The control method according to [1] or [2], wherein the azole compound is selected from the group consisting of azaconazole, bitertanol, bromuconazole, cyproconazole, difenoconazole, diniconazole, epoxyconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimenol, triticonazole, fenarimol, nuarimol, pyrifenox, imazalil, oxpoconazole fumarate, pefurazoate, prochloraz and triflumizole.

[8] The control method according to [7], wherein the azole compound is selected from the group consisting of difenoconazole, prothioconazole, triadimenol, metconazole, ipconazole, fluquinconazole, tebuconazole and triticonazole.

[9] The control method according to [8], wherein the PPO-inhibiting compound is flumioxazin, sulfentrazone or saflufenacil.

[10] The control method according to [1] or [2], wherein the strobilurin compound is selected from the group consisting of kresoxim-methyl, azoxystrobin, trifloxystrobin, fluoxastrobin, picoxystrobin, pyraclostrobin, dimoxystrobin, pyribencarb, metominostrobin, orysastrobin, enestrobin, pyraoxystrobin and pyrametostrobin.

[11] The control method according to [1] or [2], wherein the strobilurin compound is pyraclostrobin, azoxystrobin, dimoxystrobin or trifloxystrobin.

[12] The control method according to [11], wherein the PPO-inhibiting compound is flumioxazin, sulfentrazone or saflufenacil.

[13] The control method according to [1] or [2], wherein the metalaxyl compound is metalaxyl or metalaxyl-M.

[14] The control method according to [13], wherein the PPO-inhibiting compound is flumioxazin, sulfentrazone or saflufenacil.

[15] The control method according to [2], wherein the field before sowing the soybean or corn seed treated with Compound I is subjected to the step of treating with the PPO-inhibiting compound.

[16] The control method according to [2], wherein the field at sowing the soybean or corn seed treated with Compound I is subjected to the step of treating with the PPO-inhibiting compound.

[17] The control method according to [2], wherein the field after sowing the soybean or corn seed treated with Compound I is subjected to the step of treating with the PPO-inhibiting compound.

[18] The control method according to [1] or [2], wherein the noxious organisms are weeds, harmful arthropods, or plant pathogens.

[19] The control method according to [1] or [2], wherein the noxious organisms are weeds.

[20] The control method according to [2] wherein the field is the soybean field and wherein the soybean seed is treated with Compound I.

[21] The control method according to [2] wherein the field is the corn field and wherein the corn seed is treated with Compound I.

DETAILED DESCRIPTION OF EMBODIMENTS

The method for controlling noxious organisms according to the present invention includes the steps of:

(1) treating soybean or corn seeds with Compound I selected from the group consisting of neonicotinoid compounds, azole compounds, strobilurin compounds and a metalaxyl compounds, and (2) treating the field with one or more PPO inhibitor compounds selected from the group consisting of flumioxazin, sulfentrazone, saflufenacil, oxyfluorfen, and 3-(4-chloro-6-fluoro-2-trifluoromethylbenzimidazol-7-yl)-1-methyl-6-trifluoromethyl-2,4-(1H,3H)pyrimidinedione before, at or after the soybean or corn seeds treated with Compound I are sown in the field.

(1) Step of Treating Soybean or Corn Seeds with Compound I

In the present invention, the soybean seed and the corn seed are not particularly limited so long as they belong to cultivars which are generally cultivated as crop plants.

Examples of such plant cultivars include those to which resistance to herbicides has been imparted by a classical breeding method, a genetic engineering technique or the like, such herbicides being an inhibitor of 4-hydroxyphenylpyruvic acid dioxygenase (hereinafter referred to as HPPD) (e.g. isoxaflutole), an inhibitor of acetolactate synthase (hereinafter referred to as ALS)(e.g. imazethapyr, thifensulfuron-methyl), an inhibitor of 5-enolpyruvylshikimate-3-phosphate synthase (e.g. glyphosate), an inhibitor of glutamine synthase (e.g. glufosinate), an inhibitor of protoporphyrinogen oxidase (e.g. flumioxazin), an auxin type herbicide (e.g. 2,4-D, dicamba), or bromoxynil.

Examples of the crop plant to which resistance to a herbicide has been imparted by a classical breeding method include corn which is resistant to an imidazolinone type ALS inhibitor herbicide (e.g. imazethapyr) and which has already been commercially available under the trade name of Clearfield (registered trademark). Such a crop plant also includes STS soybean which is resistant to a sulfonylurea type ALS inhibitor herbicide such as thifensulfuron-methyl. Similarly, examples of the crop plant to which resistance to an acetyl CoA carboxylase inhibitor such as a trione oxime or aryloxyphenoxypropionic acid herbicide has been imparted by a classical breeding method include SR corn. Crop plants to which resistance to an acetyl CoA carboxylase inhibitor has been imparted are described in Proc. Natl. Acad. Sci. USA (1990), 87, 7175-7179.

Examples of the crop plant to which resistance to a herbicide has been imparted by a genetic engineering technique include corn cultivars and soybean cultivars, each having resistance to glyphosate, and such corn and soybean cultivars are already sold under the trade names of Roundup Ready (registered trademark), Agrisure (registered trademark) GT, and the like. Similarly, such crop plants to which resistance to a herbicide has been imparted by a genetic engineering technique include corn cultivars and soybean cultivars, each having resistance to glufosinate, and they are already sold under the trade name of LibertyLink (registered trademark), and the like. There are corn cultivars and soybean cultivars which are resistant to both glyphosate and ALS inhibitors, and they are sold under the trade name of Optimum GAT (registered trademark).

Mutant acetyl CoA carboxylase which is resistant to an acetyl CoA carboxylase inhibitor has been reported in Weed Science (2005) vol. 53, pp. 728-746, and a crop plant having resistance to an acetyl CoA carboxylase inhibitor can be produced when a gene encoding the mutant acetyl CoA carboxylase is introduced into a crop plant by a genetic engineering technique or when a mutation related to impartation of resistance is introduced into a gene encoding acetyl CoA carboxylase of a crop plant. Further, nucleic acids for introduction of a base substitution mutation can be introduced into cells of a crop plant by chimeraplasty (Gura T. 1999, Repairing the Genome's Spelling Mistakes, Science 285: 316-318) to induce a site-directed amino acid substitution mutation in the gene of acetyl CoA carboxylase or the ALS gene of the crop plant, whereby a crop plant resistant to an acetyl CoA carboxylase inhibitor or an ALS inhibitor can be produced.

A soybean crop plant resistant to dicamba can be produced by introducing a gene of dicamba-degrading enzyme such as dicamba monooxygenase isolated from *Pseudomonas maltophilia* into the plant (Behrens et al. 2007 Dicamba Resistance: Enlarging and Preserving Biotechnology-Based Weed Management Strategies. Science 316: 1185-1188).

A crop plant resistant to both a phenoxy acid herbicide (e.g. 2,4-D, MCPA, dichlorprop, or mecoprop) and an aryloxyphenoxypropionic acid herbicide (e.g. quizalofop, haloxyfop, fluazifop, dichlorfop, fenoxaprop, metamifop, cyhalofop, or clodinafop) can be produced by introducing a gene encoding an aryloxyalkanoate dioxygenase (WO 05/107437, WO 07/053482, WO 08/141154).

A crop plant resistant to HPPD inhibitors can be produced by introducing a gene encoding HPPD which shows resistance to HPPD inhibitors (US2004/0058427). A crop plant resistant to HPPD inhibitors can be produced by introducing genes encoding enzymes which caralyze HPPD-independent homogentisate synthesis (WO02/036787). A crop plant resistant to HPPD inhibitors can be produced by introducing a gene encoding over-expressing HPPD (WO96/38567). A crop plant resistant to HPPD inhibitors can be produced by introducing a gene encoding prephenate dehydrogenase to increase p-hydroxyphenylpyruvate flux in a plant over-expressing HPPD (Rippert P et. al. 2004 Engineering plant shikimate pathway for production of tocotrienol and improving herbicide resistance. Plant Physiol. 134:92-100).

Moreover, a crop plant resistant to herbicides can be produced by introducing genes described in WO98/20144, WO02/46387, and US2005/0246800.

The above-described crop plants include those to which an ability to produce a selective toxin which is known to be produced by *Bacillus*, has been imparted by a genetic engineering technique. Examples of the toxin which is produced by such a genetically engineered crop plant include insecticidal proteins derived from *Bacillus cereus* and *Bacillus popilliae*; δ-endotoxins (e.g. Cry1Ab, Cry1Ac, Cry1F, Cry1Fa2, Cry2Ab, Cry3A, Cry3Bb1 and Cry9C) and insecticidal proteins (e.g. VIP 1, VIP 2, VIP 3 and VIP 3A), derived from *Bacillus thuringiensis*; insecticidal proteins derived from nematodes; toxins produced by animals, such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, luffin, saporin, and briodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl synthase; chitinase; and glucanase; and the like.

In addition, the insecticidal toxin which is expressed in such a genetically engineered crop plant also includes hybrid toxins of δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and insecticidal proteins such as VIP 1, VIP 2, VIP 3 and VIP 3A, and toxins in which a part is deleted or modified. The hybrid toxin is made by newly combining different domains of the insecticidal proteins with use of a genetic engineering technique. Cry1Ab in which a part of an amino acid sequence is deleted is known as an example of such a toxin in which a part is deleted. An example of the toxin in which a part is modified is a toxin in which one or more of amino acids of a naturally occurring toxin are substituted. The insecticidal toxin and the genetically engineered crop plant having an ability to synthesize the insecticidal toxin are described in EP-A-0374753, WO 93/07278, WO 95/34656, EP-A-0427529, EP-A-451878, WO03/052073, and the like. Such a toxin contained in these genetically engineered crop plants imparts to a plant resistance particularly to a coleopteran pest, a dipteran pest or a lepidopteran pest.

Moreover, genetically engineered crop plants which have one or more pest-resistant genes and thereby express one or more insecticidal toxins are also known, and some of them are commercially available. Examples of such genetically engineered crop plants include YieldGard (registered trademark) (a corn cultivar expressing Cry1Ab toxin), YieldGard Rootworm (registered trademark) (a corn cultivar expressing Cry3Bb1 toxin), YieldGard Plus (registered trademark) (a corn cultivar expressing Cry1Ab and Cry3Bb1 toxins), Herculex I (registered trademark)(a corn cultivar expressing Cry1Fa2 toxin and phosphinothricin N-acetyltransferase (PAT) for imparting resistance to glufosinate), NatureGard (registered trademark) Agrisure (registered trademark) GT Advantage (a GA21 glyphosate resistant character), Agrisure (registered trademark) CB Advantage (a Bt11 corn borer (CB) character), Protecta (registered trademark), and the like.

Examples of the plant used in the present invention include a plant such as soybean having aphid resistance which is imparted by introducing, for example, the Rag 1 (Resistance Aphid Gene 1) gene.

The above-described crop plants also include those to which an ability to produce an anti-pathogen substance having a selective action has been imparted by a genetic engineering technique. The known examples of such an anti-pathogen substance are PR proteins (PRPs described in EP-A-0392225), and the like. These anti-pathogen substances and genetically engineered crop plants which produce such anti-pathogen substances are described in EP-A-0392225, WO 95/33818, EP-A-0353191, and the like. Examples of the anti-pathogen substances expressed in the genetically engineered crop plants include ion channel inhibitors such as sodium channel inhibitors and calcium channel inhibitors (KP1, KP4, KP6 toxins produced by viruses are known); stilbene synthase; bibenzyl synthase; chitinase; glucanase; PR proteins; and anti-pathogen substances produced by microorganisms, such as peptide antibiotics, heterocycle-containing antibiotics, and protein factors involved in plant disease-resistance (referred to as plant disease resistance genes and described in WO 03/000906).

The above-described crop plants include those to which a beneficial character such as a modified oil component or an enhanced amino acid content has been imparted by a genetic engineering technique. Examples of such crop plants include VISTIVE (registered trademark) (low linolenic soybean which has a reduced content of linolenic acid), and high-lysine (high-oil) corn (corn which has an increased content of lysine or oil).

Furthermore, the above-described crop plants include stacked plants which have a combination of two or more of beneficial characters such as the above-described classical herbicide-resistant character, or a herbicide-resistance gene, an insecticidal pest-resistant gene, an anti-pathogen substance-producing gene, a modified oil component, and an enhanced amino acid content.

In this step, one or more kinds of Compound I can be used.

The neonicotinoid compound of the present invention includes clothianidin, thiamethoxam, imidacloprid, dinotefuran, nitenpyram, acetamiprid, and thiacloprid.

In the present invention, an azole compound is a compound having a 5-membered heterocyclic structure containing a nitrogen atom, and usually exhibits the effect of inhibiting demethylation in the biosynthetic process of ergosterol contained in the cell membrane of eumycetes or an analogue thereof. The azole compound is also called a DMI agent (demethylation inhibitor) (see, for example, Battle Front of Development of Novel Pesticide—Development to Biological Control Science (2003) (The Frontiers of Agrobio regulators)).

The azole compound is preferably a compound selected from the group consisting of azaconazole, bitertanol, bromuconazole, cyproconazole, difenoconazole, diniconazole, epoxyconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimenol, triticonazole, fenarimol, nuarimol, pyrifenox, imazalil, oxpoconazole fumarate, pefurazoate, prochloraz and triflumizole, more preferably a compound selected from the group consisting of difenoconazole, prothioconazole, triadimenol, metconazole, ipconazole, fluquinconazole, tebuconazole and triticonazole.

The strobilurin compound is also called a QoI compound and usually exhibits plant disease control activity by acting at the Qo site of a mitochondrial electron transport complex of filamentous fungus.

The strobilurin compound is preferably a compound selected from the group consisting of kresoxim-methyl azoxystrobin, trifloxystrobin, fluoxastrobin, picoxystrobin, pyraclostrobin, dimoxystrobin, pyribencarb, metominostrobin, orysastrobin, enestrobin, pyraoxystrobin and pyrametostrobin, more preferably pyraclostrobin, azoxystrobin, dimoxystrobin or trifloxystrobin, further preferably pyraclostrobin, azoxystrobin or trifloxystrobin.

The metalaxyl compound usually exhibits the effect of controlling plant diseases caused by filamentous fungus. The metalaxyl compound is preferably metalaxyl or metalaxyl-M. Metalaxyl-M is also called mefenoxam.

In the control method of the present invention, Compound I is preferably one or more neonicotinoid compounds selected from the group consisting of clothianidin, thiamethoxam, imidacloprid, dinotefuran, nitenpyram, acetamiprid and thiacloprid.

In the step of treating soybean or a corn seeds with Compound I, Compound I is usually mixed with a solid carrier or a liquid carrier, formulated with optional addition of an auxiliary agent for formulation, such as surfactants, and then used. Compound I can be formulated by conventional methods. Examples of the solid carriers, liquid carriers and auxiliary agents include what are generally used for the formulation.

The dosage of Compound I used for treating soybean or corn seeds is usually in the range of 0.001 to 40 g per 1 kg of seeds, preferably 0.01 to 10 g per 1 kg of seeds. The method for applying Compound I to plant seeds includes, for example, a method of subjecting seeds to dust coating with a formulation containing Compound I, a method of immersing seeds in a formulation containing Compound I, and a method of coating seeds with a carrier containing Compound I.

In the method of immersing seeds in a formulation containing Compound I, the concentration of Compound I in the formulation is preferably 10 to 700000 ppm, more preferably 100 to 100000 ppm.

(2) Step of Treating the Field with at Least One PPO Inhibitor Before, at or After the Soybean or Corn Seeds Treated with Compound I are Sown in the Field The PPO inhibitor compound is a herbicidal compound which inhibits protoporphillinogen IX oxidase (EC1.3.3.4) located on a chlorophyll synthesis pathway in plant plastids, thereby causing withering and death of the plant.

The PPO inhibitor compound of the present invention is selected from the group consisting of flumioxazin, sulfentrazone, saflufenacil, oxyfluorfen, and 3-(4-chloro-6-fluoro-2-trifluoromethylbenzimidazol-7-yl)-1-methyl-6-trifluoromethyl-2,4-(1H,3H)pyrimidinedione, and preferbably flumioxazin, sulfentrazone or saflufenacil, and more preferbably flumioxazin.

In this step, one or more kinds of PPO inhibitor compounds can be used.

In the step of treating the field with the PPO inhibitor compound, such a PPO inhibitor compound is usually mixed with a solid carrier or a liquid carrier, formulated with optional addition of an auxiliary agent for formulation, such as surfactants, and then used. PPO inhibitor compounds can be formulated by conventional methods. Examples of the solid carriers, liquid carriers and auxiliary agents include what are generally used for the formulation.

Examples of the method of treating the field with a PPO inhibitor compound include a method of applying a PPO inhibitor compound to the soil of the field, and a method of applying a PPO inhibitor compound to weeds after their germination.

The dosage of the PPO inhibitor compound used in this step is usually 5 to 2000 g, preferably 5 to 500 g, per 10,000 m$^2$. In the step, an adjuvant may be mixed at the time of such treatment with the PPO inhibitor compound.

The soybean or corn seeds which have been treated with Compound I are sown in a field by a conventional method. In the method for controlling noxious organisms according to the present invention, the PPO inhibitor compound may be applied before sowing soybean or corn seeds, may be applied at sowing soybean or corn seeds or may be applied after sowing soybean or corn seeds.

In the case where the PPO inhibitor compound is applied before sowing soybean or corn seeds, the PPO inhibitor compound is applied 50 days before to immediately before the sowing, preferably 30 days before to immediately before the sowing, more preferably 20 days before to immediately before the sowing.

In the case where the PPO inhibitor compound is applied at sowing soybean or corn seeds, the PPO inhibitor compound is applied at the same time of the sowing.

In the case where the PPO inhibitor compound is applied after sowing soybean or corn seeds, the PPO inhibitor compound is applied preferably immediately after to 50 days after the sowing, more preferably immediately after to 3 days after the sowing. Concrete treatment time in the treatment with the PPO inhibitor compound after sowing soybean seeds includes, for example, the time from pre-emergence of soybean to flowering time. The time from pre-emergence of soybean to flowering time is preferably the time from pre-emergence of soybean to a stage of 6 compound leaves, and more preferably the time from pre-emergence of soybean to a stage of 3 compound leaves. Concrete treatment time in the treatment with the PPO inhibitor compound after sowing corn seeds includes the time from pre-emergence of corn to 12 leaf stage, preferably the time from pre-emergence of corn to 8 leaf stage, and more preferably the time from pre-emergence of corn to 6 leaf stage. The leaf age of corn is determined by the leaf collar method.

In the present invention, the above-mentioned PPO-inhibiting compounds are preferably applied to soil or weeds in the field where soybean or corn seeds treated with Compound I have been sown or where the seeds are to be sown. One embodiment of the present invention is a control method against noxious organisms in a field of soybean or corn, which comprises applying one or more PPO-inhibiting compounds selected from the group consisting of flumioxazin, sulfentrazone, saflufenacil, oxyfluorfen and 3-(4-chloro-6-fluoro-2-trifluoromethylbenzimidazol-7-yl)-1-methyl-6-trifluoromethyl-2,4-(1H,3H)pyrimidinedione to soil or weeds in the field where soybean or corn seeds have been sown or where the seeds are to be sown, said seeds being treated with one or more compounds selected from the group consisting of neonicotinoid compounds, azole compounds, strobilurin compounds and metalaxyl compounds.

According to the method for controlling noxious organisms of the present invention, weeds in the field of soybean or corn can be controlled.

Examples of such weeds include the followings.

Polygonaceae weeds: *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicus, Rumex crispus, Rumex obtusifolius, Rumex acetosa,*

Portulaceae seeds: *Portulaca oleracea,*

Caryophyllaceae weeds: *Stellaria media, Cerastium holosteoides, Cerastium glomeratum, Spergula arvensis,*

Chenopodiaceae weeds: *Chenopodium album, Kochia scoparia, Salsola kali, Atriplex* spp., Amaranthaceae weeds: *Amaranthus retroflexus, Amaranthus viridis, Amaranthus lividus, Amaranthus spinosus, Amaranthus hybridus, Amaranthus palmeri, Amaranthus rudis, Amaranthus patulus, Amaranthus tuberculatos, Amaranthus blitoides, Alternanthera philoxeroides, Alternanthera sessilis,*

Papaveraceae weeds: *Papaver rhoeas,*

Cruciferae weeds: *Raphanus raphanistrum, Sinapis arvensis, Capsella bursa*-pastoris, *Brassica juncea, Descurainia pinnata, Rorippa islandica, Rorippa sylvestris, Thlaspi arvense,*

Leguminosae weeds: *Aeschynomene indica, Sesbania exaltata, Cassia obtusifolia, Cassia occidentalis, Desmodium tortuosum, Trifolium repens, Pueraria lobata, Vicia angustifolia,*

Oxalidaceae weeds: *Oxalis corniculata, Oxalis strica,*

Geraniaceae weeds: *Geranium carolinense, Erodium cicutarium,*

Euphorbiaceae weeds: *Euphorbia helioscopia, Euphorbia maculata, Euphorbia humistrata, Euphorbia esula, Euphorbia heterophylla, Acalypha australis,*

Malvaceae weeds: *Abutilon theophrasti, Sida spinosa, Hibiscus trionum,*

Violaceae weeds: *Viola arvensis, Viola tricolor,*

Cucurbitaceae weeds: *Sicyos angulatus, Echinocystis lobata,*

Lythraceae weeds: *Lythrum salicaria,*

Apiaceae weeds: *Hydrocotyle sibthorpioides,*

Asclepiadaceae weeds: *Asclepias syriaca, Ampelamus albidus*

Rubiaceae weeds: *Galium aparine, Galium spurium* var. echinospermon, *Spermacoce latifolia,*

Convolvulaceae weeds: *Ipomoea nil, Ipomoea hederacea, Ipomoea purpurea, Ipomoea hederacea* var. *integriuscula, Ipomoea lacunosa, Ipomoea triloba, Ipomoea coccinea, Ipomoea quamoclit, Convolvulus arvensis, Calystegia hederacea,*

Boraginaceae weeds: *Myosotis arvensis,*

Lamiaceae weeds: *Lamium purpureum, Lamium amplexicaule,*

Solanaceae weeds: *Datura stramonium, Solanum nigrum, Solanum americanum, Solanum ptycanthum, Solanum sarrachoides, Solanum rostratum, Solanum aculeatissimum, Solanum carolinense, Physalis angulata, Physalis subglabrata, Nicandra physaloides,*

Scrophulariaceae weeds: *Veronica hederaefolia, Veronica persica, Veronica arvensis,*

Plantaginaceae weeds: *Plantago asiatica,*

Compositae weeds: *Xanthium pensylvanicum, Xanthium occidentale, Helianthus annuus, Matricaria chamomilla, Matricaria perforata, Chrysanthemum segetum, Matricaria matricarioides, Artemisia princeps, Solidago altissima, Taraxacum officinale, Galinsoga ciliata, Senecio vulgaris, Conyza bonariensis, Conyza canadensis, Ambrosia artemisiaefolia, Ambrosia trifida, Bidens pilosa, Bidens frondosa, Cirsium arvense, Cirsium vulgare, Carduus nutans, Lactuca serriola, Sonchus asper,*

Liliaceae weeds: *Allium canadense, Allium vineale,*

Commelinaceae weeds: *Commelina communis, Commelina bengharensis,*

Poaceae weeds: *Echinochloa crus*-galli, *Setaria viridis, Setaria faberi, Setaria glauca, Digitaria ciliaris, Digitaria sanguinalis, Eleusine indica, Poa annua, Alospecurus aequalis, Alopecurus myosuroides, Avena fatua, Sorghum halepense, Sorghum vulgare, Agropyron repens, Lolium multiflorum, Lolium perenne, Lolium rigidum, Bromus secalinus, Bromus tectorum, Hordeum jubatum, Aegilops cylindrica, Phalaris arundinacea, Phalaris minor, Apera spica*-venti, *Panicum dichotomiflorum, Panicum texanum, Brachiaria platyphylla, Cenchrus echinatus, Cenchrus pauciflorus, Eriochloa villosa,*

Cyperaceae weeds: *Cyperus microiria, Cyperus iria, Cyperus rotundus, Cyperus esculentus, Kyllinga gracillima,*

Equisetaceae weeds: *Equisetum arvense, Equisetum palustre,* and the like.

When one or more neonicotinoid compounds are used as Compound I, harmful arthropods in the field of soybean or corn can be controlled by the method of the present invention.

Examples of such harmful arthropods include the followings.

Hemipteran pests: planthoppers such as *Laodelphax striatellus, Nilaparvata lugens,* and *Sogatella furcifera,* leafhoppers such as *Nephotettix cincticeps,* and *Nephotettix virescens,* aphids such as *Aphis gossypii, Myzus persicae, Brevicoryne brassicae, Macrosiphum euphorbiae, Aulacorthum solani, Rhopalosiphum padi,* and *Toxoptera citricidus,* plant bugs such as *Nezara antennata, Riptortus clavetus, Leptocorisa chinensis, Eysarcoris parvus, Halyomorpha mista,* and *Lygus lineolaris,* whiteflies such as *Trialeurodes vaporariorum, Bemisia tabaci,* and *Bemisia argentifolii,* scales such as *Aonidiella aurantii, Comstockaspis perniciosa, Unaspis citri, Ceroplastes rubens,* and *Icerya purchasi,* lace bugs, jumping plantlices, and the like;

Lepidopteran pests: Pyralidae such as *Chilo suppressalis, Tryporyza incertulas, Cnaphalocrocis medinalis, Notarcha derogata, Plodia interpunctella, Ostrinia furnacalis, Ostrinia nubilaris, Hellula undalis,* and *Pediasia teterrellus,* Noctuidae such as *Spodoptera litura, Spodoptera exigua, Pseudaletia separata, Mamestra brassicae, Agrotis ipsilon, Plusia nigrisigna, Trichoplusia* spp., *Heliothis* spp., and *Helicoverpa* spp., Pieridae such as *Pieris rapae,* Adoxophyes spp., Tortricidae such as *Grapholita molesta, Leguminivora glycinivorella, Matsumuraeses azukivora, Adoxophyes orana fasciata, Adoxophyes* sp., *Homona magnanima, Archips fuscocupreanus,* and *Cydia pomonella,* Gracillariidae such as *Caloptilia theivora,* and *Phyllonorycter ringoneella,* Carposinidae such as *Carposina niponensis,* Lyonetiidae such as *Lyonetia* spp., Lymantriidae spp., Lymantriidae such as *Euproctis* spp., Yponameutidae such as *Plutella xylostella,* Gelechiidae such as *Pectinophora gossypiella,* and *Phthorimaea operculella,* Arctiidae such as *Hyphantria cunea,* Tineidae such as *Tinea translucens,* and *Tineola bisselliella,* and the like;

Thysanopteran pests: Thripidae such as *Frankliniella occidentalis, Thrips parmi, Scirtothrips dorsalis, Thrips tabaci, Frankliniella intonsa,* and *Frankliniella fusca,* and the like;

Dipteran pests: Agromyzidae such as *Musca domestica, Culex popiens pallens, Tabanus trigonus, Hylemya antiqua, Hylemya platura, Anopheles sinensis, Agromyza oryzae, Hydrellia griseola, Chlorops oryzae,* and *Liriomyza trifolii, Dacus cucurbitae, Ceratitis capitata,* and the like;

Coleopteran pest: *Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serricorne, Anthrenus verbasci, Tribolium castaneum, Lyctus brunneus, Anoplophora malasiaca, Tomicus piniperda,* and the like;

Orthopteran pests: *Locusta migratoria, Gryllotalpa africana, Oxya yezoensis, Oxya japonica,* and the like;

Hymenopteran pests: *Athalia rosae, Acromyrmex* spp., *Solenopsis* spp., and the like;

Blattaria pests: *Blattella germanica, Periplaneta fuliginosa, Periplaneta americana, Periplaneta brunnea, Blatta orientalis,* and the like;

Acarina pests: Tetranychidae such as *Tetranychus urticae, Panonychus citri,* and *Oligonychus* spp., Eriophyidae such as *Aculops pelekassi,* Tarsonemidae such as *Polyphagotarsonemus latus,* Tenuipalpidae, Tuckerellidae, Acaridae such as *Tyrophagus putrescentiae,* Dermanyssidae such as *Dermatophagoides farinae,* and *Dermatophagoides ptrenyssnus,* Cheyletidae such as *Cheyletus eruditus, Cheyletus malaccensis,* and *Cheyletus moorei,* and the like.

When one or more azole compounds are used as Compound I, plant pathogens in the field of soybean or corn can be controlled by the method of the present invention.

Examples of such plant pathogens include the followings. *Cercospora kikuchii, Microsphaera diffusa, Diaporthe phaseolorum* var. sojae, *Septoria glycines, Cercospora sojina, Phakopsora pachyrhizi, Rhizoctonia solani, Sclerotinia sclerotiorum, Cercospora zeae*-maydis, *Rhizoctonia solani.*

When one or more strobilurin compounds are used as Compound I, plant pathogens in the field of soybean or corn can be controlled by the method of the present invention.

Examples of such plant pathogens include the followings. *Cercospora kikuchii, Elsinoe glycines, Diaporthe phaseolorum* var. sojae, *Septoria glycines, Cercospora sojina, Phakopsora pachyrhizi, Phytophthora sojae, Rhizoctonia solani, Sclerotinia sclerotiorum, Ustilago maydis,*

*Cochliobolus heterostrophus, Gloeocercospora sorghi, Puccinia polysora, Cercospora zeae*-maydis, *Rhizoctonia solani, Aspergillus, Penicillium, Fusarium, Gibberella, Tricoderma, Thielaviopsis, Rhizopus, Mucor, Corticium, Phoma, Rhizoctonia, Diplodia*.

When one or more metalaxyl analogues are used as Compound I, plant pathogens in the field of soybean or corn can be controlled by the method of the present invention.

Examples of such plant pathogens include the followings. *Peronospora manshurica, Phyotophthora sojae, Pythium* spp., *Sclerophthora rayssiae, Aphanomyces*.

In the method for controlling noxious organisms according to the present invention, one or more other agricultural chemicals may be used in combination. Such other agricultural chemicals include, for example, insecticides, acaricides, nematicides, fungicides, herbicides, plant growth regulators, and safeners.

Examples of such other agricultural chemicals include the followings.

Insecticides: fenthion, fenitrothion, pirimiphos-methyl, diazinon, quinalphos, isoxathion, *Pyridafenthion, chlorpyrifos*-methyl, vamidothion, malathion, phenthoate, dimethoate, disulfoton, monocrotophos, tetrachlorvinphos, chlorfenvinphos, propaphos, acephate, trichlorphon, EPN, pyraclorfos, carbaryl, metolcarb, isoprocarb, BPMC, propoxur, XMC, carbofuran, carbosulfan, benfuracarb, furathiocarb, methomyl, thiodicarb, cycloprothrin, ethofenprox, cartap, bensultap, thiocyclam, buprofezin, tebufenozide, ethiprole, and pyridalyl.

Acaricides: hexythiazox, pyridaben, fenpyroximate, tebufenpyrad, chlorfenapyr, etoxazole, pyrimidifen, and spirodiclofen.

Nematicides: fosthiazate.

Fungicides: captan, IBP, EDDP, tolclofos-methyl, benomyl, carbendazim, thiophanate-methyl, mepronil, flutolanil, thifluzamid, furametpyr, teclofthalam, pencycuron, carpropamid, diclocymet, metalaxyl, triflumizole, azaconazole, bromuconazole, cyproconazole, diclobutrazol, difenoconazole, diniconazole, Mdiniconazole-M, epoxiconazole, fenbuconazole, fluquinconazole, flusilazole, flutriafol, furconazole, furconazole-cis, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, pefurazoate, prochloraz, azoxystrobin, dimoxystrobin, fluoxastrobin, kresoximmethyl, metominostrobin, orysastrobin, picoxystrobin, pyraclostrobin, trifloxystrobin, validamycinA, blasticidin S, kasugamycin, polyoxin, fthalide, probenazole, isoprothiolane, tricyclazole, pyroquilon, ferimzone, acibnzolar S-methyl, diclomezine, oxolinic acid, phenazine oxide, TPN, and iprodione.

Herbicides: dicamba, 2,4-D, 2,4-DB, MCPA, MCPB, mecoprop, Pmecoprop-P, dichlorprop, Pdichlorprop-P, bromoxynil, dichlobenil, ioxynil, di-allate, butylate, tri-allate, phenmedipham, chlorpropham, asulam, phenisopham, benthiocarb, molinate, esprocarb, pyributicarb, prosulfocarb, orbencarb, EPTC, dimepiperate, swep, propachlor, metazachlor, alachlor, acetochlor, metolachlor, S-metolachlor, butachlor, pretilachlor, thenylchlor, aminocyclopyrachlor, trifluralin, pendimethalin, ethalfluralin, benfluralin, prodiamine, simazine, atrazine, propazine, cyanazine, ametryn, simetryn, dimethmetryn, prometryn, indaziflam, triaziflam, metribuzin, hexazinone, isoxaben, diflufenican, diuron, linuron, fluometuron, difenoxuron, methyl-daimuron, isoproturon, isouron, tebuthiuron, benzthiazuron, methabenzthiazuron, propanil, mefenacet, clomeprop, naproanilide, bromobutide, daimuron, cumyluron, diflufenzopyr, etobenzanid, bentazon, tridiphane, indanofan, amitrole, fenchlorazole, clomazone, maleic hydrazide, pyridate, chloridazon, norflurazon, bromacil, terbacil, oxaziclomefone, cinmethylin, benfuresate, cafenstrole, pyrithiobac, pyrithiobac-sodium, pyriminobac, pyriminobac-methyl, bispyribac, bispyribac-sodium, pyribenzoxim, pyrimisulfan, pyriftalid, fentrazamide, dimethenamid, dimethenamid-P, ACN, bennzobicyclon, dithiopyr, triclopyr, thiazopyr, aminopyralid, clopyralid, dalapon, chlorthiamid, amidosulfuron, azimsulfuron, bensulfuron, bensulfuron-methyl, chlorimuron, chlorimuronethyl, cyclosulfamuron, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, mesosulfuron, mesosulfuron-methyl, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron, chlorsulfuron, cinosulfuron, ethametsulfuron, ethametsulfuron-methyl, iodosulfuron, iodosulfuron-methyl-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, picolinafen, beflubutamid, mesotrione, sulcotrione, tefuryltrione, tembotrione, isoxachlortole, isoxaflutole, benzofenap, pyrasulfotole, pyrazolynate, pyrazoxyfen, topramezone, flupoxam, amicarbazone, bencarbazone, flucarbazone, flucarbazone-sodium, ipfencarbazone, propoxycarbazone, propoxycarbazone-sodium, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium, imazapic, imazapic-ammonium, imazapyr, imazaquin, imazethapyr, clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, pinoxaden, pyroxasulfone, glyphosate, glyphosate-isopropylamine, glyphosate-trimethylsulfonium, glyphosate-ammonium, glyphosate-diammonium, glyphosate-sodium, glyphosate-potassium, glufosinate, glufosinate-ammonium, glufosinate-P, glufosinate-P-sodium, bialafos, anilofos, bensulide, butamifos, paraquat, and diquat.

Plant growth regulators: hymexazol, paclobutrazol, uniconazole, uniconazole-P, inabenfide, prohexadione-calcium, 1-methylcyclopropene, trinexapac, and gibberellins.

Safeners: benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, and oxabetrinil.

EXAMPLES

The present invention will be illustrated by the following examples, but the present invention is not limited to these examples. In addition, ha in the following descriptions means hectare, i.e. 10,000 m$^2$.

First of all, evaluation criteria for an insecticidal effect, a herbicidal effect, and phytotoxicity described in the following examples are shown.

[Insecticidal Effect]

The evaluation of the insecticidal effect was performed by determining the life and death of the insects at the time of the investigation and calculating the protective value according to the following equation;

Protective Value (%)=100×(1−T/C)

wherein the symbols have the following meanings;

C: The number of insects at the time of observation in an untreated section: and T: The number of insects at the time of observation in a treated section.

[Herbicidal Effect and Phytotoxicity]

The herbicidal effect is evaluated using a scale of 0 to 100, wherein a score of "0" means that there is no or little difference in the degree of germination or growth in test weeds between treated weeds and untreated weeds at the time of observation, and a score of "100" means that the test weeds result in complete withering and death or their germination or growth is completely inhibited.

The phytotoxicity against crop plants is evaluated by using "no harm", "low", "moderate" or "high", wherein "no harm" means that no or little phytotoxicity is found, "low" means that a slight degree of phytotoxicity is found, "moderate" means that a medium degree of phytotoxicity is found, and "high" means that a severe degree of phytotoxicity is found. The "phytotoxicity" herein evaluated means the symptoms of injury which have been judged to be attributable to the compound being applied, not the symptoms of injury caused by noxious organisms, and this difference should be clearly distinguished.

Example 1

In a plastic cup of 96 mm in inside diameter and 44 mm in height, 24.5 μL of a clothianidin suspension (a suspension containing 20% of clothianidin, trade name: Dantotsu Flowable, manufactured by Sumitomo Chemical Co., Ltd.) and 50 soybean seeds were placed. The plastic cup was shaken by the hand so that the clothianidin suspension was attached to the soybean seeds.

A soil in admixture with about 500 mg each of the seeds of *Portulaca oleracea*, *Amaranthus retroflexus* and *Polygonum lapathifolium* was packed in a plastic pot of 177 mm in inside diameter and 140 mm in height. The above soybean seeds were sown in this pot at a rate of two seeds per pot. On the day of sowing soybean seeds and after the sowing, an aqueous diluted solution (55.8 ppm or 111.6 ppm) of a flumioxazin water dispersible granule (a water dispersible granule containing 51% of flumioxazin, trade name: Valor SX, manufactured by Valent USA Corp.) was uniformly sprayed on the soil surface with a sprayer so as to apply the dosage given in the table.

Thereafter, the test pot was placed in a greenhouse. On day 15 after soybean sowing, 20 larvae and imagos of *Aulacorthum solani* alive on a soybean leaf were placed in the pot and the whole plant was covered with a nylon cloth.

On day 6 after release of *Aulacorthum solani*, the insecticidal effect, herbicidal effect, and phytotoxicity were examined. The insecticidal effect is shown in Table 1 and the herbicidal effect and phytotoxicity are shown in Table 2.

TABLE 1

| Clothianidin Treatment | Flumioxazin Treatment | Protective Value |
|---|---|---|
| None | 12.5 g/ha | 0 |
| None | 25 g/ha | 0 |
| 44.7 g/ha | None | 59.1 |
| 44.7 g/ha | 12.5 g/ha | 76.4 |
| 44.7 g/ha | 25 g/ha | 71.2 |

TABLE 2

| Clothianidin Treatment | Flumioxazin Treatment | Evaluation of Effect on Weeds | Phytotoxicity to Soybean |
|---|---|---|---|
| 44.7 g/ha | 12.5 g/ha | 100 | No harm |
| 44.7 g/ha | 25 g/ha | 100 | No harm |

Example 2

In a plastic cup of 96 mm in inside diameter and 44 mm in height, 31.4 μL of a thiamethoxam formulation (a formulation containing 30% of thiamethoxam, trade name: CRUISER FS30, manufactured by Syngenta Japan KK) and 50 soybean seeds were placed. The plastic cup was shaken by the hand so that the thiamethoxam formulation was attached to the soybean seeds.

A soil in admixture with about 500 mg each of the seeds of *Portulaca oleracea*, *Amaranthus retroflexus* and *Polygonum lapathifolium* was packed in a plastic pot of 177 mm in inside diameter and 140 mm in height. The above soybean seeds were sown in this pot at a rate of two seeds per pot. On the day of sowing soybean seeds and after the sowing, an aqueous diluted solution (223.2 ppm) of a flumioxazin water dispersible granule (a water dispersible granule containing 51% of flumioxazin, trade name: Valor SX, manufactured by Valent USA Corp.) was uniformly sprayed on the soil surface with a sprayer so as to apply the dosage given in the table.

Thereafter, the test pot was placed in a greenhouse. On day 15 after soybean sowing, 20 larvae and imagos of *Aulacorthum solani* alive on a soybean leaf were placed in the pot and the whole pot was covered with a nylon cloth.

On day 6 after release of *Aulacorthum solani*, the insecticidal effect, herbicidal effect, and phytotoxicity were investigated. The insecticidal effect is shown in Table 3 and the herbicidal effect and phytotoxicity are shown in Table 4.

TABLE 3

| Thiamethoxam Treatment | Flumioxazin Treatment | Protective Value |
|---|---|---|
| None | 50 g/ha | 0 |
| 78.9 g/ha | None | 86.9 |
| 78.9 g/ha | 50 g/ha | 100 |

TABLE 4

| Thiamethoxam Treatment | Flumioxazin Treatment | Evaluation of Effect on Weeds | Phytotoxicity to Soybean |
|---|---|---|---|
| 78.9 g/ha | 50 g/ha | 100 | No harm |

Example 3

In a plastic cup of 96 mm in inside diameter and 44 mm in height, 16.0 µL, of a clothianidin suspension (a suspension containing 20% of clothianidin, trade name: Dantotsu Flowable, manufactured by Sumitomo Chemical Co., Ltd.) and 50 soybean seeds were placed. The plastic cup was shaken by the hand so that the clothianidin suspension was attached to the soybean seeds.

A soil in admixture with about 500 mg each of the seeds of *Spergula arvensis*, *Portulaca oleracea* and *Amaranthus retroflexus* was packed in a plastic pot of 177 mm in inside diameter and 140 mm in height. The above soybean seeds were sown in this pot at a rate of two seeds per pot. On the day of sowing soybean seeds and after the sowing, an aqueous diluted solution (892.9 ppm) of a sulfentrazone dry flowable formulation (a dry flowable formulation containing 75% of sulfentrazone, trade name: Cover 75 DF, manufactured by Du Pont) was uniformly sprayed on the soil surface with a sprayer so as to apply the dosage given in the table.

Thereafter, the test pot was placed in a greenhouse. On day 14 after soybean sowing, 20 larvae and imagos of *Aulacorthum solani* alive on a soybean leaf were placed in the pot and the whole pot was covered with a nylon cloth.

On day 7 after release of *Aulacorthum solani*, the insecticidal effect, herbicidal effect, and phytotoxicity were examined. The insecticidal effect is shown in Table 5 and the herbicidal effect and phytotoxicity are shown in Table 6.

TABLE 5

| Clothianidin Treatment | Sulfentrazone Treatment | Protective Value |
|---|---|---|
| None | 200 g/ha | 0 |
| 55.3 g/ha | None | 55.2 |
| 55.3 g/ha | 200 g/ha | 88.7 |

TABLE 6

| Clothianidin Treatment | Sulfentrazone Treatment | Evaluation of Effect on Weeds | Phytotoxicity to Soybean |
|---|---|---|---|
| 55.3 g/ha | 200 g/ha | 100 | No harm |

Example 4

In a plastic cup of 96 mm in inside diameter and 44 mm in height, 108.8 µL, of a clothianidin suspension (a suspension containing 20% of clothianidin, trade name: Dantotsu Flowable, manufactured by Sumitomo Chemical Co., Ltd.) and 30 corn seeds were placed. The plastic cup was shaken by the hand so that the clothianidin suspension was attached to the corn seeds. In addition, the clothianidin suspension was attached to the corn seeds in a similar manner except that it was used in an amount of 217.5 µL.

A soil in admixture with about 500 mg each of the seeds of *Spergula arvensis*, *Portulaca oleracea* and *Amaranthus retroflexus* was packed in a plastic pot of 177 mm in inside diameter and 140 mm in height. The above corn seeds were sown in this pot at a rate of two seeds per pot. On the day of sowing corn seeds and after the sowing, an aqueous diluted solution (66.6 ppm or 223.2 ppm) of a flumioxazin water dispersible granule (a water dispersible granule containing 51% of flumioxazin, trade name: Valor SX, manufactured by Valent USA Corp.) was uniformly sprayed on the soil surface with a sprayer so as to apply the dosage given in the table.

Thereafter, the test pot was placed in a greenhouse. On day 22 after corn sowing, 10 fourth-instar larvae of *Spodoptera litura* were released in the pot and the whole pot was then covered with a nylon cloth.

On day 3 after release of *Spodoptera litura*, the insecticidal effect was examined.

In addition, on day 22 after corn sowing, the herbicidal effect and phytotoxicity were examined.

The insecticidal effect is shown in Table 7, and the herbicidal effect and phytotoxicity are shown in Table 8.

TABLE 7

| Clothianidin Treatment | Flumioxazin Treatment | Protective Value |
|---|---|---|
| None | 12.5 g/ha | 0 |
| None | 50 g/ha | 5 |
| 553 g/ha | None | 30 |
| 984 g/ha | None | 65 |
| 553 g/ha | 12.5 g/ha | 100 |
| 553 g/ha | 50 g/ha | 100 |
| 984 g/ha | 12.5 g/ha | 100 |
| 984 g/ha | 50 g/ha | 100 |

TABLE 8

| Clothianidin Treatment | Flumioxazin Treatment | Evaluation of Effect on Weeds | Phytotoxicity to Corn |
|---|---|---|---|
| 553 g/ha | 12.5 g/ha | 100 | No harm |
| 553 g/ha | 50 g/ha | 100 | No harm |
| 984 g/ha | 12.5 g/ha | 100 | No harm |
| 984 g/ha | 50 g/ha | 100 | No harm |

Example 5

In a plastic cup of 96 mm in inside diameter and 44 mm in height, 108.8 µL of a clothianidin suspension (a suspension containing 20% of clothianidin, trade name: Dantotsu Flowable, manufactured by Sumitomo Chemical Co., Ltd.) and 30 corn seeds were placed. The plastic cup was shaken by the hand so that the clothianidin suspension was attached to the corn seeds. In addition, the clothianidin suspension was attached to the corn seeds in a similar manner except that it was used in an amount of 217.5 µL.

A soil in admixture with about 500 mg each of the seeds of *Polygonum lapathifolium*, *Amaranthus retroflexus* and *Portulaca oleracea* was packed in a plastic pot of 177 mm in inside diameter and 140 mm in height. The above corn seeds were sown in this pot at a rate of one seed per pot. On the day of sowing corn seeds and after the sowing, an aqueous diluted solution (64 ppm or 250 ppm) of saflufenacil was uniformly sprayed on the soil surface with a sprayer so as to apply the dosage given in the table. The aqueous diluted solution of saflufenacil was prepared by dissolving a given amount of saflufenacil in acetone containing 2% (w/v) of Tween 20, and diluting this solution with water to an acetone concentration of 10% (v/v).

Thereafter, the test pot was placed in a greenhouse. On day 22 after corn sowing, 10 fourth-instar larvae of *Spodoptera litura* were released in the pot and the whole pot was then covered with a nylon cloth.

On day 3 after release of *Spodoptera litura*, the insecticidal effect was examined.

In addition, on day 22 after corn sowing, the herbicidal effect and phytotoxicity were examined.

The insecticidal effect is shown in Table 9, and the herbicidal effect and phytotoxicity are shown in Table 10.

TABLE 9

| Clothianidin Treatment | Saflufenacil Treatment | Protective Value |
|---|---|---|
| None | 32 g/ha | 0 |
| None | 125 g/ha | 0 |
| 272 g/ha | None | 30 |
| 496 g/ha | None | 40 |
| 272 g/ha | 32 g/ha | 80 |
| 272 g/ha | 125 g/ha | 100 |
| 496 g/ha | 32 g/ha | 90 |
| 496 g/ha | 125 g/ha | 100 |

TABLE 10

| Clothianidin Treatment | Saflufenacil Treatment | Evaluation of Effect on Weeds | Phytotoxicity to Corn |
|---|---|---|---|
| 272 g/ha | 32 g/ha | 100 | No harm |
| 272 g/ha | 125 g/ha | 100 | No harm |
| 496 g/ha | 32 g/ha | 100 | No harm |
| 496 g/ha | 125 g/ha | 100 | No harm |

Example 6

In a plastic cup of 96 mm in inside diameter and 44 mm in height, 11.1 µL of a clothianidin suspension (a suspension containing 20% of clothianidin, trade name: Dantotsu Flowable, manufactured by Sumitomo Chemical Co., Ltd.) and 20 soybean seeds were placed. The plastic cup was shaken by the hand so that the clothianidin suspension was attached to the soybean seeds.

A soil was packed in a 1/5000a Wagner pot. The above soybean seeds were sown in the Wagner pot at a rate of two seeds per pot, and the seeds of *Ipomoea hederacea* were sown in the pot at a rate of three seeds per pot. On the day of sowing soybean seeds and after the sowing, a flumioxazin granule (a granule containing 0.25% of flumioxazin, trade name: BroadStar, manufactured by Valent USA Corp.) were uniformly scattered on the soil surface by the hand so as to apply the dosage given in Table 11.

On day 11 after sowing of the seeds of soybean and *Ipomoea hederacea*, the herbicidal effect and phytotoxicity were examined.

The herbicidal effect and phytotoxicity are shown in Table 11.

TABLE 11

| Clothianidin Treatment | Flumioxazin Treatment | Evaluation of Effect on Weeds | Phytotoxicity to Soybean |
|---|---|---|---|
| 73 g/ha | None | 0 | No harm |
| None | 25 g/ha | 25 | No harm |
| 73 g/ha | 25 g/ha | 85 | No harm |

Example 7

In a plastic cup of 96 mm in inside diameter and 44 mm in height, 108.75 µL of a clothianidin suspension (a suspension containing 20% of clothianidin, trade name: Dantotsu Flowable, manufactured by Sumitomo Chemical Co., Ltd.) and 30 corn seeds were placed. The plastic cup was shaken by the hand so as to attach the clothianidin suspension to the corn seeds.

A soil was packed in a 1/5000a Wagner pot. The above corn seeds were sown in the Wagner pot at a rate of one seed per pot, and the seeds of *Ipomoea hederacea* were sown in the pot at a rate of three seeds per pot. On the day of sowing corn seeds and after the sowing, an aqueous diluted solution (100 ppm) of saflufenacil was uniformly drenched on the soil surface with a pipette so as to apply the dosage given in the table. The aqueous diluted solution of saflufenacil was prepared by dissolving a given amount of saflufenacil in acetone containing 2% (w/v) of Tween 20, and diluting this solution with water to an acetone concentration of 10% (v/v).

On day 11 after sowing of the seeds of corn and *Ipomoea hederacea*, the herbicidal effect and phytotoxicity were examined.

The herbicidal effect and phytotoxicity are shown in Table 12.

TABLE 12

| Clothianidin Treatment | Saflufenacil Treatment | Evaluation of Effect on Weeds | Phytotoxicity to Corn |
|---|---|---|---|
| 340 g/ha | None | 0 | No harm |
| 605 g/ha | None | 0 | No harm |
| None | 32 g/ha | 50 | No harm |
| 340 g/ha | 32 g/ha | 100 | No harm |
| 605 g/ha | 32 g/ha | 100 | No harm |

Example 8

Clothianidin is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 9

Clothianidin is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 10

Thiamethoxam is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 11

Thiamethoxam is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 12

Clothianidin is attached to soybean seeds and corn seeds. Then, a soil is packed in a pot, and the above seeds and weed seeds are sown. On the day of sowing, sulfentrazone is uniformly applied to the soil surface. The pot is placed in a greenhouse.

On day 10 after sowing, the herbicidal effect against the weeds is examined. As a result, a control effect against the weeds can be confirmed.

Example 13

Thiamethoxam is attached to soybean seeds and corn seeds. Then, a soil is packed in a pot, and the above seeds and weed seeds are sown. On the day of sowing, flumioxazin is uniformly applied to the soil surface. The pot is placed in a greenhouse.

On day 10 after sowing, the herbicidal effect against the weeds is examined. As a result, a control effect against the weeds can be confirmed.

Example 14

Thiamethoxam is attached to soybean seeds and corn seeds. Then, a soil is packed in a pot, and the above seeds and weed seeds are sown. On the day of sowing, sulfentrazone is uniformly applied to the soil surface. The pot is placed in a greenhouse.

On day 10 after sowing, the herbicidal effect against the weeds is examined. As a result, a control effect against the weeds can be confirmed.

Example 15

Thiamethoxam is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 16

In a glass container measuring 60 mm in inner diameter and 20 mm in height, 8 μl of a prothioconazole emulsifiable concentrate (emulsifiable concentrate containing 25% prothioconazole, manufactured by Bayer Crop Science Inc. under the trade name of Proline) and 20 corn seeds were placed. The prothioconazole emulsifiable concentrate was adhered to the corn seeds by shaking this plastic cup by hand. In the same manner, 8 μl of a difenoconazole emulsifiable concentrate (emulsifiable concentrate containing 25% difenoconazole, manufactured by Syngenta under the trade name of Score) was adhered to 20 corn seeds. In the same manner, 50 mg of a tebuconazole suspension (suspension containing 20% tebuconazole, manufactured by Hokko Chemical Industry under the trade name of ONLY ONE Flowable) was adhered to 20 corn seeds.

A plastic pot measuring 194 mm in inner diameter and 176 mm in height was filled with the soil. In this pot, 3 corn seeds were sown per 1 pot and 10 seeds of *Ipomoea hederacea* were sown per 1 pot. On the day of sowing of the corn seeds, after sowing the corn seeds, a water diluted solution (24.5 mg of product/liter) of a flumioxazin granular wettable powder (granular wettable powder containing 51% flumioxazin, manufactured by Valent USA Corporation under the trade name of Valor SX) and a water diluted solution (15 mg/liter) of saflufenacil were uniformly sprayed over a surface of the soil in each amount described in Tables 13 to 18, using a sprayer. The water diluted solution of saflufenacil was prepared by dissolving a predetermined amount of saflufenacil in acetone containing 2% (w/v) Tween 20 and diluting the solution with water so as to adjust the concentration to 10% by volume.

Twelve days after sowing the seeds of corn and *Ipomoea hederacea*, herbicidal activity was examined.

Herbicidal activity is shown in Tables 13 to 18.

TABLE 13

| Prothioconazole Treatment | Flumioxazin Treatment | Herbicidal activity on *Ipomoea hederacea* |
|---|---|---|
| None | 50 g/ha | 88 |
| 102 g/ha | 50 g/ha | 100 |

TABLE 14

| Difenoconazole Treatment | Flumioxazin Treatment | Herbicidal activity on *Ipomoea hederacea* |
|---|---|---|
| None | 50 g/ha | 88 |
| 102 g/ha | 50 g/ha | 98 |

TABLE 15

| Tebuconazole Treatment | Flumioxazin Treatment | Herbicidal activity on *Ipomoea hederacea* |
|---|---|---|
| None | 50 g/ha | 88 |
| 508 g/ha | 50 g/ha | 100 |

TABLE 16

| Prothioconazole Treatment | Saflufenacil Treatment | Herbicidal activity on *Ipomoea hederacea* |
|---|---|---|
| None | 30 g/ha | 88 |
| 102 g/ha | 30 g/ha | 100 |

TABLE 17

| Difenoconazole Treatment | Saflufenacil Treatment | Herbicidal activity on *Ipomoea hederacea* |
|---|---|---|
| None | 30 g/ha | 88 |
| 102 g/ha | 30 g/ha | 100 |

TABLE 18

| Tebuconazole Treatment | Saflufenacil Treatment | Herbicidal activity on *Ipomoea hederacea* |
|---|---|---|
| None | 30 g/ha | 88 |
| 508 g/ha | 30 g/ha | 99 |

Example 17

Prothioconazole is attached to soybean seeds. Then, a soil is packed in a pot, and the above seeds and weed seeds are sown. On the day of sowing, flumioxazin is uniformly applied to the soil surface. The pot is placed in a greenhouse.

On day 10 after sowing, the herbicidal effect against the weeds is examined. As a result, a control effect against the weeds can be confirmed.

Example 18

Difenoconazole is attached to soybean seeds. Then, a soil is packed in a pot, and the above seeds and weed seeds are sown. On the day of sowing, flumioxazin is uniformly applied to the soil surface. The pot is placed in a greenhouse.

On day 10 after sowing, the herbicidal effect against the weeds is examined. As a result, a control effect against the weeds can be confirmed.

Example 19

Tebuconazole is attached to soybean seeds. Then, a soil is packed in a pot, and the above seeds and weed seeds are sown. On the day of sowing, flumioxazin is uniformly applied to the soil surface. The pot is placed in a greenhouse.

On day 10 after sowing, the herbicidal effect against the weeds is examined. As a result, a control effect against the weeds can be confirmed.

Example 20

Ipconazole is attached to soybean seeds and corn seeds. Then, a soil is packed in a pot, and the above seeds and weed seeds are sown. On the day of sowing, flumioxazin is uniformly applied to the soil surface. The pot is placed in a greenhouse.

On day 10 after sowing, the herbicidal effect against the weeds is examined. As a result, a control effect against the weeds can be confirmed.

Example 21

Triadimenol is attached to soybean seeds and corn seeds. Then, a soil is packed in a pot, and the above seeds and weed seeds are sown. On the day of sowing, flumioxazin is uniformly applied to the soil surface. The pot is placed in a greenhouse.

On day 10 after sowing, the herbicidal effect against the weeds is examined. As a result, a control effect against the weeds can be confirmed.

Example 22

Metconazole is attached to soybean seeds and corn seeds. Then, a soil is packed in a pot, and the above seeds and weed seeds are sown. On the day of sowing, flumioxazin is uniformly applied to the soil surface. The pot is placed in a greenhouse.

On day 10 after sowing, the herbicidal effect against the weeds is examined. As a result, a control effect against the weeds can be confirmed.

Example 23

Fluquinconazole is attached to soybean seeds and corn seeds. Then, a soil is packed in a pot, and the above seeds and weed seeds are sown. On the day of sowing, flumioxazin is uniformly applied to the soil surface. The pot is placed in a greenhouse.

On day 10 after sowing, the herbicidal effect against the weeds is examined. As a result, a control effect against the weeds can be confirmed.

Example 24

Triticonazole is attached to soybean seeds and corn seeds. Then, a soil is packed in a pot, and the above seeds and weed seeds are sown. On the day of sowing, flumioxazin is uniformly applied to the soil surface. The pot is placed in a greenhouse.

On day 10 after sowing, the herbicidal effect against the weeds is examined. As a result, a control effect against the weeds can be confirmed.

Example 25

Prothioconazole is attached to soybean seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 26

Difenoconazole is attached to soybean seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 27

Tebuconazole is attached to soybean seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 28

Ipconazole is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 29

Triadimenol is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 30

Metconazole is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 31

Fluquinconazole is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 32

Triticonazole is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 33

Prothioconazole is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 34

Difenoconazole is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 35

Tebuconazole is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 36

Ipconazole is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 37

Triadimenol is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 38

Metconazole is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 39

Fluquinconazole is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 40

Triticonazole is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 41

Prothioconazole is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 42

Difenoconazole is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 43

Tebuconazole is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 44

Ipconazole is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 45

Triadimenol is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 46

Metconazole is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 47

Fluquinconazole is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 48

Triticonazole is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 49

Prothioconazole is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 50

Difenoconazole is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 51

Tebuconazole is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 52

Ipconazole is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 53

Triadimenol is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 54

Metconazole is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 55

Fluquinconazole is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 56

Triticonazole is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 57

Difenoconazole, prothioconazole, triadimenol, metconazole, ipconazole, fluquinconazole, tebuconazole or triticonazole is adhered to soybean seeds. Then, a pot is filled with the contaminated soil made by mixing with *Rhizoctonia solani* Kuhn and the seeds are sown. On the day of sowing, a surface of the soil is uniformly treated with flumioxazin, sulfentrazone, saflufenacil, oxyfluorfen or 3-(4-chloro-6-fluoro-2-trifluoromethylbenzimidazol-7-yl)-1-methyl-6-trifluoromethyl-2,4-(1H,3H)pyrimidinedione. This pot is placed in a greenhouse.

Fourteen to twenty-eight days after sowing, the healthy population is examined. As a result, the control effect against *Fusarium oxysporum* f. sp. can be confirmed.

Example 58

In a plastic cup measuring 65 mm in inner diameter and 75 mm in height, 4.8 mg of a pyraclostrobin emulsifiable concentrate (emulsifiable concentrate containing 23.8% pyraclostrobin, manufactured by BASF under the trade name of Comet) and 12 soybean seeds were placed. The pyraclostrobin emulsifiable concentrate was adhered to the soybean seeds by shaking this plastic cup by hand. In the same manner, 13.2 mg of the pyraclostrobin emulsifiable concentrate was adhered to the soybean seeds. In the same manner, 4.8 mg of an azoxystrobin suspension (emulsifiable concentrate containing 22.9% azoxystrobin, manufactured by Syngenta under the trade name of Amistar) was adhered to the soybean seeds. In the same manner, 20.4 mg of an azoxystrobin suspension was adhered to the soybean seeds.

A water diluted solution of a trifloxystrobin granular wettable powder (2.6%) was prepared by adding 52 mg of a trifloxystrobin granular wettable powder (granular wettable powder containing 50% trifloxystrobin, manufactured by Bayer Crop Science Inc. under the trade name of Flint) to 1 mL of desalted water. 51.6 mg of this water diluted solution and 12 soybean seeds were placed in the plastic cup. The water diluted solution of trifloxystrobin was adhered to the soybean seeds by shaking this plastic cup by hand. In the same manner, 199.2 mg of the water diluted solution of trifloxystrobin was adhered to the soybean seeds.

A plastic pot measuring 194 mm in inner diameter and 176 mm in height was filled with the soil. In this pot, 2 soybean seeds were sown per 1 pot and 10 seeds of *Ipomoea hederacea* var. integriuscula and *Senna obtusifolia* were sown per 1 pot. On the day of sowing of the soybean seeds, after sowing the soybean seed, a flumioxazin granule (granule containing 0.25% flumioxazin, manufactured by Valent USA Corporation under the trade name of BroadStar) was uniformly scattered over a surface of the soil in the amount described in Tables 19 to 21 by hand.

Twelve days after sowing the seeds of soybean, *Ipomoea hederacea* var. integriuscula and *Senna obtusifolia*, herbicidal activity was examined.

Herbicidal activity is shown in Tables 19 to 21.

TABLE 19

| | | Herbicidal activity | |
| --- | --- | --- | --- |
| Pyraclostrobin Treatment | Flumioxazin Treatment | *Ipomoea hederacea* var. *integriuscula* | *Senna obtusifolia* |
| None | 25 g/ha | 25 | 20 |
| None | 100 g/ha | 85 | 45 |
| 65 g/ha | 100 g/ha | 100 | 90 |
| 178 g/ha | 25 g/ha | 80 | 55 |

TABLE 20

| | | Herbicidal activity | |
| --- | --- | --- | --- |
| Azoxystrobin Treatment | Flumioxazin Treatment | *Ipomoea hederacea* var. *integriuscula* | *Senna obtusifolia* |
| None | 25 g/ha | 25 | 20 |
| None | 100 g/ha | 85 | 45 |
| 62 g/ha | 100 g/ha | 100 | 93 |
| 264 g/ha | 25 g/ha | 70 | 60 |

TABLE 21

| | | Herbicidal activity | |
|---|---|---|---|
| Trifloxystrobin Treatment | Flumioxazin Treatment | Ipomoea hederacea var. integriuscula | Senna obtusifolia |
| None | 25 g/ha | 25 | 20 |
| None | 100 g/ha | 85 | 45 |
| 76 g/ha | 100 g/ha | 95 | 83 |
| 293 g/ha | 25 g/ha | 80 | 75 |

Example 59

In a glass container measuring 60 mm in inner diameter and 20 mm in height, 8 mg of a pyraclostrobin emulsifiable concentrate (emulsifiable concentrate containing 23.8% pyraclostrobin, manufactured by BASF under the trade name of Comet) and 25 corn seeds were placed. After capping a glass container, the pyraclostrobin emulsifiable concentrate was adhered to the corn seeds by shaking the glass container by hand. In the same manner, 22 mg of the pyraclostrobin emulsifiable concentrate was adhered to the corn seeds.

A plastic pot measuring 194 mm in inner diameter and 176 mm in height was filled with the soil. In this pot, 2 corn seeds were sown per 1 pot and 10 seeds of *Ipomoea lacunosa* were sown per 1 pot. On the day of sowing of the corn seeds, after sowing the corn seeds, a water diluted solution (24.5 mg of product/liter) of a flumioxazin granular wettable powder (granular wettable powder containing 51% flumioxazin, manufactured by Valent USA Corporation under the trade name of Valor SX), a water diluted solution (66.7 mg of product/liter) of a sulfentrazone granular wettable powder (granular wettable powder containing 75% sulfentrazone, manufactured by FMC Corporation under the trade name of Cover), a water diluted solution (15 mg/liter) of saflufenacil and a water diluted solution (100 mg/liter) of oxyfluorfen were uniformly sprayed over a surface of the soil in each amount described in Tables 22 to 25, using a sprayer. The water diluted solutions of saflufenacil and oxyfluorfen were prepared by dissolving each predetermined amount of saflufenacil and oxyfluorfen in acetone containing 2% (w/v) Tween 20 and diluting each solution with water so as to adjust the concentration of acetone to 10% by volume.

Twelve days after sowing the seeds of corn and *Ipomoea lacunose*, herbicidal activity was examined.

Herbicidal activity is shown in Tables 22 to 25.

TABLE 22

| Pyraclostrobin Treatment | Flumioxazin Treatment | Herbicidal activity |
|---|---|---|
| None | 25 g/ha | 40 |
| 52 g/ha | 25 g/ha | 65 |
| 142 g/ha | 25 g/ha | 75 |

TABLE 23

| Pyraclostrobin Treatment | Sulfentrazone Treatment | Herbicidal activity |
|---|---|---|
| None | 100 g/ha | 40 |
| 142 g/ha | 100 g/ha | 80 |

TABLE 24

| Pyraclostrobin Treatment | Saflufenacil Treatment | Herbicidal activity |
|---|---|---|
| None | 30 g/ha | 45 |
| 142 g/ha | 30 g/ha | 75 |

TABLE 25

| Pyraclostrobin Treatment | Oxyfluorfen Treatment | Herbicidal activity |
|---|---|---|
| None | 200 g/ha | 45 |
| 52 g/ha | 200 g/ha | 75 |

Example 60

Pyraclostrobin is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 61

Azoxystrobin is attached to soybean seeds and corn seeds. Then, a soil is packed in a pot, and the above seeds and weed seeds are sown. On the day of sowing, sulfentrazone is uniformly applied to the soil surface. The pot is placed in a greenhouse.

On day 10 after sowing, the herbicidal effect against the weeds is examined. As a result, a control effect against the weeds can be confirmed.

Example 62

Azoxystrobin is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 63

Azoxystrobin is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 64

Azoxystrobin is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 65

Dimoxystrobin is attached to soybean seeds and corn seeds. Then, a soil is packed in a pot, and the above seeds and weed seeds are sown. On the day of sowing, flumioxazin is uniformly applied to the soil surface. The pot is placed in a greenhouse.

On day 10 after sowing, the herbicidal effect against the weeds is examined. As a result, a control effect against the weeds can be confirmed.

Example 66

Dimoxystrobin is attached to soybean seeds and corn seeds. Then, a soil is packed in a pot, and the above seeds and weed seeds are sown. On the day of sowing, sulfentrazone is uniformly applied to the soil surface. The pot is placed in a greenhouse.

On day 10 after sowing, the herbicidal effect against the weeds is examined. As a result, a control effect against the weeds can be confirmed.

Example 67

Dimoxystrobin is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 68

Dimoxystrobin is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 69

Dimoxystrobin is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 70

Trifloxystrobin is attached to soybean seeds and corn seeds. Then, a soil is packed in a pot, and the above seeds and weed seeds are sown. On the day of sowing, sulfentrazone is uniformly applied to the soil surface. The pot is placed in a greenhouse.

On day 10 after sowing, the herbicidal effect against the weeds is examined. As a result, a control effect against the weeds can be confirmed.

Example 71

Trifloxystrobin is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 72

Trifloxystrobin is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 73

Trifloxystrobin is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 74

Pyraclostrobin, azoxystrobin, dimoxystrobin or trifloxystrobin is attached to soybean seeds. Then, a soil is packed in a pot, and the above seeds and weed seeds are sown. On the day of sowing, flumioxazin, sulfentrazone, saflufenacil, oxyfluorfen or 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

At the time when primary leaf of *Glycine max* is observed, a spore suspension of *Phakopsora pachyrhizi* Sydow is spray-inoculated, followed by humidification overnight. Fourteen to twelve-eight days after sowing, the lesion area is examined. As a result, the control effect against *Phakopsora pachyrhizi* can be confirmed.

Example 75

In a glass container measuring 60 mm in inner diameter and 20 mm in height, 12 mg of a metalaxyl emulsifiable concentrate (emulsifiable concentrate containing 25% metalaxyl, manufactured by Syngenta under the trade name of Subdue) and 20 soybean seeds were placed. After capping this glass container, the metalaxyl emulsifiable concentrate was adhered to the soybean seeds by shaking the glass container by hand. In the same manner, 47 mg of the metalaxyl emulsifiable concentrate was adhered to the soybean seeds. In the same manner, 9 mg of a metalaxyl-M emulsifiable concentrate (emulsifiable concentrate containing 33.3% metalaxyl-M manufactured by Syngeta under the trade name of Apron XL) was adhered to the soybean seeds. In the same manner, 40 mg of the metalaxyl-M emulsifiable concentrate was adhered to the soybean seeds.

A plastic pot measuring 194 mm in inner diameter and 176 mm in height was filled with the soil. In this pot, 2 soybean seeds were sown per 1 pot, 7 seeds of *Ipomoea hederacea* were sown per 1 pot, and 10 seeds of *Digitaria ciliaris* were sown per 1 pot. On the day of sowing of the soybean seeds, after sowing the soybean seeds, a water diluted solution (49 mg of product/liter) of a flumioxazin granular wettable powder (granular wettable powder containing 51% flumioxazin, manufactured by Valent USA Corporation under the trade name of Valor SX) was uniformly sprayed over a surface of the soil in each amount described in Tables 1 to 2, using a sprayer.

Twelve days after sowing the seeds of soybean, *Ipomoea hederacea* and *Digitaria ciliaris*, herbicidal activity was examined.

Herbicidal activity is shown in Tables 26 to 27.

TABLE 26

| Metalaxyl Treatment | Flumioxazin Treatment | Herbicidal activity | |
|---|---|---|---|
| | | *Ipomoea hederacea* | *Digitaria ciliaris* |
| None | 50 g/ha | 55 | 75 |
| 102 g/ha | 50 g/ha | 85 | 99 |
| 398 g/ha | 50 g/ha | 95 | 97 |

TABLE 27

| Metalaxyl-M Treatment | Flumioxazin Treatment | Herbicidal activity | |
|---|---|---|---|
| | | *Ipomoea hederacea* | *Digitaria ciliaris* |
| None | 50 g/ha | 55 | 75 |
| 102 g/ha | 50 g/ha | 85 | 99 |
| 451 g/ha | 50 g/ha | 97 | 99 |

Example 76

In a glass container measuring 60 mm in inner diameter and 20 mm in height, 15 mg of a metalaxyl-M emulsifiable concentrate (emulsifiable concentrate containing 33.3% metalaxyl-M, manufactured by Syngeta under the trade name of Apron XL) and 25 corn seeds were placed. After capping this glass container, the metalaxyl-M emulsifiable concentrate was adhered to the corn seeds by shaking the glass container by hand. In the same manner, 33 mg of the metalaxyl-M emulsifiable concentrate was adhered to the corn seeds.

A plastic pot measuring 194 mm in inner diameter and 176 mm in height was filled with the soil. In this pot, 2 corn seeds were sown per 1 pot and 10 seeds of *Ipomoea lacunosa* were sown per 1 pot. On the day of sowing of the corn seeds, after sowing the corn seeds, a water diluted solution (24.5 mg of product/liter) of a flumioxazin granular wettable powder (granular wettable powder containing 51% flumioxazin, manufactured by Valent USA Corporation under the trade name of Valor SX), a water diluted solution (66.7 mg of product/liter) of a sulfentrazone granular wettable powder (granular wettable powder containing 75% sulfentrazone manufactured by FMC Corporation under the trade name of Cover), a water diluted solution (15 mg/liter) of saflufenacil and a water diluted solution (100 mg/liter) of oxyfluorfen were uniformly sprayed over a surface of the soil in each amount described in Tables 28 to 31, using a sprayer. The water diluted solutions of saflufenacil and oxyfluorfen were prepared by dissolving each predetermined amount of saflufenacil and oxyfluorfen in acetone containing 2% (w/v) Tween 20 and diluting each solution with water so as to adjust the concentration of acetone to 10% by volume.

Ten days after sowing the seeds of corn and *Ipomoea lacunosa*, herbicidal activity was examined.

Herbicidal activity is shown in Tables 28 to 31.

TABLE 28

| Metalaxyl-M Treatment | Flumioxazin Treatment | Herbicidal activity |
|---|---|---|
| None | 25 g/ha | 40 |
| 135 g/ha | 25 g/ha | 88 |
| 298 g/ha | 25 g/ha | 75 |

TABLE 29

| Metalaxyl-M Treatment | Sulfentrazone Treatment | Herbicidal activity |
|---|---|---|
| None | 100 g/ha | 40 |
| 135 g/ha | 100 g/ha | 90 |
| 298 g/ha | 100 g/ha | 70 |

TABLE 30

| Metalaxyl-M Treatment | Saflufenacil Treatment | Herbicidal activity |
|---|---|---|
| None | 30 g/ha | 45 |
| 135 g/ha | 30 g/ha | 98 |
| 298 g/ha | 30 g/ha | 75 |

TABLE 31

| Metalaxyl-M Treatment | Oxyfluorfen Treatment | Herbicidal activity |
|---|---|---|
| None | 200 g/ha | 45 |
| 298 g/ha | 200 g/ha | 75 |

Example 77

Metalaxyl is attached to soybean seeds and corn seeds. Then, a soil is packed in a pot, and the above seeds and weed seeds are sown. On the day of sowing, sulfentrazone is uniformly applied to the soil surface. The pot is placed in a greenhouse.

On day 10 after sowing, the herbicidal effect against the weeds is examined. As a result, a control effect against the weeds can be confirmed.

Example 78

Metalaxyl is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Example 79

Metalaxyl is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 80

Metalaxyl is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 81

Metalaxyl or Metalaxyl-M is attached to corn seeds. Then, a soil contaminated with *Phytophthora megasperma* is packed in a pot, and the above seeds are sown. On the day of sowing, flumioxazin, sulfentrazone, saflufenacil, oxyfluorfen or 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

Fourteen to twelve-eight days after sowing, the lesion area is examined. As a result, the control effect against *Phytophthora megasperma* can be confirmed.

INDUSTRIAL AVAILABILITY

Noxious organisms in the fields of soybean or corn can be controlled by the method for controlling noxious organisms according to the present invention.

The invention claimed is:

1. A control method against noxious organisms in a field of soybean or corn, which comprises applying one or more PPO-inhibiting compounds selected from the group consisting of flumioxazin, sulfentrazone, and saflufenacil to soil or weeds in the field where soybean or corn seeds have been sown or where said seeds are to be sown, said seeds being treated with a Compound I, which is one or more compounds selected from the group consisting of neonicotinoid insecticides, azole fungicides, strobilurin fungicides and metalaxyl compounds;
wherein the azole fungicide is selected from the group consisting of difenoconazole, prothioconazole, and tebuconazole; and
wherein the combination of the one or more PPO-inhibiting compounds and the Compound I has improved herbicidal activity over each compound alone.

2. A control method against noxious organisms in a field of soybean or corn, which comprises the steps of:
treating soybean or corn seeds with a Compound I selected from the group consisting of neonicotinoid insecticides, azole fungicides, strobilurin fungicides and metalaxyl compounds, and
treating the field with one or more PPO-inhibiting compounds selected from the group consisting of flumioxazin, sulfentrazone, and saflufenacil before, at or after sowing the soybean or corn seed treated with the Compound I;
wherein the azole fungicide is selected from the group consisting of difenoconazole, prothioconazole, and tebuconazole; and
wherein the combination of the one or more PPO-inhibiting compounds and the Compound I has improved herbicidal activity over each compound alone.

3. The control method according to claim 1 or 2, wherein the neonicotinoid insecticide is selected from the group consisting of clothianidin, thiamethoxam, imidacloprid, dinotefuran, nitenpyram, acetamiprid and thiacloprid.

4. The control method according to claim 2 wherein the Compound I is one or more neonicotinoid insecticides selected from the group consisting of clothianidin, thiamethoxam, imidacloprid, dinotefuran, nitenpyram, acetamiprid and thiacloprid.

5. The control method according to claim 1 or 2, wherein the neonicotinoid insecticide is clothianidin or thiamethoxam.

6. The control method according to claim 1 or 2, wherein the strobilurin fungicide is selected from the group consisting of kresoxim-methyl, azoxystrobin, trifloxystrobin, fluoxastrobin, picoxystrobin, pyraclostrobin, dimoxystrobin, pyribencarb, metominostrobin, orysastrobin, enestrobin, pyraoxystrobin and pyrametostrobin.

7. The control method according to claim 1 or 2, wherein the strobilurin fungicide is pyraclostrobin, azoxystrobin, dimoxystrobin or trifloxystrobin.

8. The control method according to claim 2, wherein the field before sowing the soybean or corn seed treated with the Compound I is subjected to the step of treating the field with the PPO-inhibiting compound.

9. The control method according to claim 2, wherein the field at sowing the soybean or corn seed treated with the Compound I is subjected to the step of treating the field with the PPO-inhibiting compound.

10. The control method according to claim 2, wherein the field after sowing the soybean or corn seed treated with the Compound I is subjected to the step of treating the field with the PPO-inhibiting compound.

11. The control method according to claim 1 or 2, wherein the noxious organisms are weeds, harmful arthropods, or plant pathogens.

12. The control method according to claim 1 or 2, wherein the noxious organisms are weeds.

13. The control method according to claim 2 wherein the field is the soybean field and wherein the soybean seed is treated with the Compound I.

14. The control method according to claim 2 wherein the field is the corn field and wherein the corn seed is treated with the Compound I.

15. A control method against noxious organisms in a field of soybean or corn, which comprises applying one or more PPO-inhibiting compounds selected from the group consisting of flumioxazin, sulfentrazone, and saflufenacil to soil or weeds in the field where soybean or corn seeds have been sown or where said seeds are to be sown, said seeds being treated with a Compound I, which is one or more compounds selected from the group consisting of neonicotinoid insecticides, azole fungicides, strobilurin fungicides and metalaxyl compounds;
  wherein the metalaxyl compound is metalaxyl or metalaxyl-M; and
  wherein the combination of the one or more PPO-inhibiting compounds and the Compound I has improved herbicidal activity over each compound alone.

16. A control method against noxious organisms in a field of soybean or corn, which comprises:
  treating soybean or corn seeds with a Compound I selected from the group consisting of neonicotinoid insecticides, azole fungicides, strobilurin fungicides and metalaxyl compounds, and
  treating the field with one or more PPO-inhibiting compounds selected from the group consisting of flumioxazin, sulfentrazone, and saflufenacil before, at or after sowing the soybean or corn seed treated with the Compound I;
  wherein the metalaxyl compound is metalaxyl or metalaxyl-M; and
  wherein the combination of the one or more PPO-inhibiting compounds and the Compound I has improved herbicidal activity over each compound alone.

17. A control method against noxious organisms in a field of soybean or corn, which comprises applying one or more PPO-inhibiting compounds selected from the group consisting of flumioxazin, sulfentrazone, and saflufenacil to soil or weeds in the field where soybean or corn seeds have been sown or where said seeds are to be sown, said seeds being treated with a Compound I, which is one or more compounds selected from the group consisting of azole fungicides and metalaxyl compounds;
  wherein the azole fungicide is selected from the group consisting of difenoconazole, prothioconazole, and tebuconazole, and the metalaxyl compound is metalaxyl or metalaxyl-M; and
  wherein the combination of the one or more PPO-inhibiting compounds and the Compound I has improved herbicidal activity over each compound alone.

18. A control method against noxious organisms in a field of soybean or corn, which comprises the steps of:
  treating soybean or corn seeds with a Compound I selected from the group consisting of azole fungicides and metalaxyl compounds, and
  treating the field with one or more PPO-inhibiting compounds selected from the group consisting of flumioxazin, sulfentrazone, and saflufenacil before, at or after sowing the soybean or corn seed treated with the Compound I;
  wherein the azole fungicide is selected from the group consisting of difenoconazole, prothioconazole, and tebuconazole, and the metalaxyl compound is metalaxyl or metalaxyl-M; and
  wherein the combination of the one or more PPO-inhibiting compounds and the Compound I has improved herbicidal activity over each compound alone.

* * * * *